United States Patent [19]

Koenig

[11] 4,133,863

[45] Jan. 9, 1979

[54] COLLECTION TUBE ASSEMBLY AND METHOD FOR COLLECTING BIOLOGICAL FLUIDS

[75] Inventor: Elmer A. Koenig, Arlington Heights, Ill.

[73] Assignee: Sherwood Medical Industries, Inc., St. Louis, Mo.

[21] Appl. No.: 780,282

[22] Filed: Mar. 23, 1977

[51] Int. Cl.² ........................ A61M 5/00; B01L 3/00
[52] U.S. Cl. .................... 422/99; 422/102; 422/50; 23/230 B; 128/2 F; 128/DIG. 5
[58] Field of Search ........ 128/218 P, 218 D, DIG. 5, 128/2 F; 23/259, 292; 73/425.6

[56] References Cited

U.S. PATENT DOCUMENTS

| | | | |
|---|---|---|---|
| 3,318,021 | 5/1967 | Sarnoff | 128/218 D |
| 3,782,197 | 1/1974 | Grams | 73/421 R |
| 3,885,549 | 5/1975 | Green | 128/2 F |
| 3,930,492 | 1/1976 | Hatsuno et al. | 128/2 F |
| 3,976,069 | 8/1976 | Ong | 128/218 D |

*Primary Examiner*—Morris O. Wolk
*Assistant Examiner*—Michael S. Marcus
*Attorney, Agent, or Firm*—Gardner & Anten

[57] ABSTRACT

An improved fluid collection tube assembly, particularly adapted for collecting blood or other biological fluid, includes a plastic collection tube having a forward end closed by a rubber diaphragm and an open rear end. A resilient piston member is slidably disposed within the tube in sealing engagement with the interior wall of the tube and is spaced forwardly from the open rear end. Prior to collecting a biological fluid from a patient, ambient air is in the space between the closed forward end of the tube and the piston member. When it is desired to collect a biological fluid from a patient, the piston is drawn rearwardly into the rear end of the tube to create a vacuum in the tube between the rubber diaphragm and the piston member.

2 Claims, 9 Drawing Figures

4,133,863

COLLECTION TUBE ASSEMBLY AND METHOD FOR COLLECTING BIOLOGICAL FLUIDS

FIELD OF THE INVENTION

The present invention relates to an improved fluid collection tube assembly for collecting blood or other biological fluid from a patient.

BACKGROUND OF THE INVENTION

Clinical evaluation of biological fluids, such as blood, has long been an important procedure in the examination and treatment of individuals seeking medical attention. For example, it is conventional, in medical practice, to withdraw a blood sample from a patient into a collection tube. Thereafter, the blood sample is subjected to laboratory procedures (e.g., centrifugal separation of the blood sample into plasma or serum and cells) and analysis.

In recent years the tubes provided for collecting blood have been glass tubes which are evacuated or vacuumized by the manufacturer and used in conjunction with a device having a double-ended needle cannula. Typically, such a collection tube comprises an impervious glass tube having one end permanently closed (e.g., by an integral, semi-spherical portion of the glass tube) and the other end closed by a rubber stopper or diaphragm which is adapted to be punctured and penetrated by one end of a double-ended needle cannula. In use, one end of the double-ended needle cannula is inserted into the patient's vein and the stoppered end of the tube is thrust onto the other end of the needle cannula so as to pierce the stopper or diaphragm. Since the tube is evacuated or vacuumized, blood from the patient is thereby sucked into the collection tube.

Examples of evacuated or vacuumized glass collection tubes of the type described above are shown in U.S. Pat. Nos. 2,460,641 and 3,771,965.

Processing of the blood in glass collection tubes by laboratory personnel has been found, in some instances, to give rise to the transfer of disease (e.g., hepatitis) or infection to personnel handling such tubes. Disease transference or infection may occur if the glass tube breaks and the blood contacts the hands or other body parts of the handling personnel. In addition, contamination to the personnel may occur in the transferring of collected blood or other biological fluids to another container or to processing apparatus due to the aerosol action of the blood being processed.

Another disadvantage associated with the use of glass collection tubes is that they are relatively expensive.

The problems associated with the cost of glass tubes and the transference of disease due to breakage of blood-filled tubes could be eliminated by employing a nonbreakable tube, such as plastic, for example, In the past, however, plastic tubes were thought to be unacceptable because they could not maintain a vacuum over an extended period of time, i.e., from the time of evacuation or vacuumization by the manufacturer until the tube is actually employed to collect a fluid sample. It is recognized that plastic is not as impervious to air as glass, and during the storage time between evacuation by the manufacturer and use, air can migrate through the plastic and the connection between the plastic tube and the rubber stopper thereto to destroy or partially destroy any vacuum in the tube.

The problems of contamination of laboratory personnel and possible disease transference arising from processing of blood samples after collection are addressed in U.S. Pat. No. 3,782,197. That patent proposes a blood collection tube provided with a resilient piston member in the bottom of the tube for forcing collected blood into another container for subsequent analysis. However, the collection tube of the U.s. Pat. No. 3,782,197 is designed to be evacuated or vacuumized by the manufacturer, and thus does not solve the breakage problems and other problems and costs associated with glass collection tubes.

OBJECTS AND SUMMARY OF THE INVENTION

In view of the foregoing, it is an object of the present invention to provide an improved fluid collection tube assembly which obviates the disadvantages and problems associated with prior art fluid collection tube assemblies.

A more specific object of the present invention is to provide a fluid collection tube assembly which may be manufactured of nonbreakable material, such as plastic.

Another object of the present invention is the provision of an improved fluid collection tube assembly which need not be vacuumized by the manufacturer, but which may be vacuumized quickly and easily prior to collecting of a fluid sample from a patient.

Still another object of the present invention is the provision of an improved fluid collection tube assembly which is adapted to both collect blood or other biological fluids from patients and to dispense the collected blood for subsequent processing and/or analysis without the need for removing a stopper member.

The foregoing, and other objects and advantages of the present invention have been realized by the provision of a fluid collection tube assembly comprising a tube, which may be manufactured of a nonbreakable material, such as plastic, for example, having a forward end closed by a cannula-puncturable stopper member and an open rear end. A piston member is disposed within the tube in sliding sealing engagement with the interior wall of the tube. Prior to collecting a fluid specimen from a patient, the piston member is drawn rearwardly in the tube into the open rear end thereof to create a vacuum in the tube to facilitate collection of the fluid specimen. Drawing the piston member rearwardly into the open rear end of the tube may be accomplished by utilizing a tool to pull the piston member rearwardly or by subjecting the rear end of the tube to a source of vacuum to draw the piston member rearwardly.

DETAILED DESCRIPTION OF PREFERRED EMBODIMENTS

Figure 1:
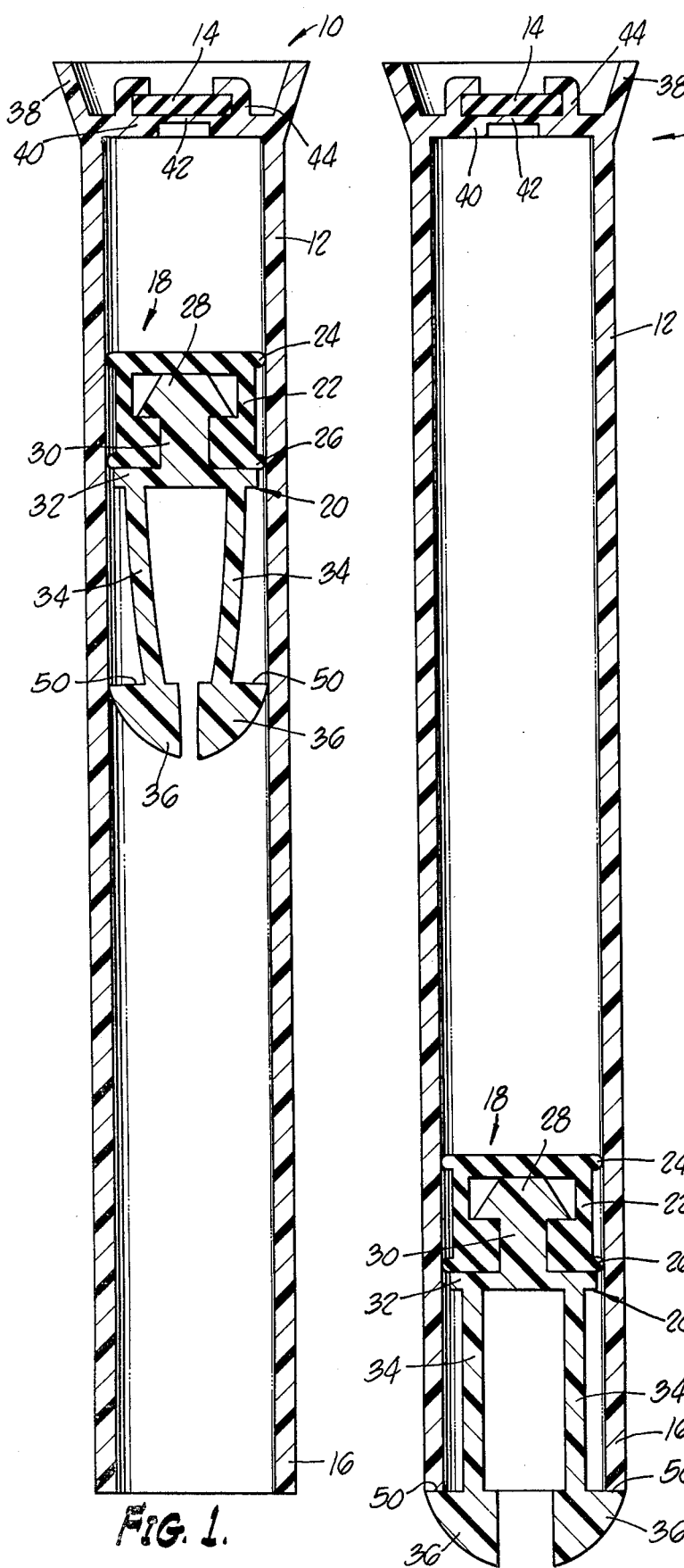
FIG. 1 is a sectional elevation view of an improved fluid collection tube assembly constructed in accordance with the teachings of the present invention, with the piston member of the assembly being shown disposed within the tube, near the closed forward end thereof, prior to being drawn into the rear end to create a vacuum in the tube.
Figure 2:
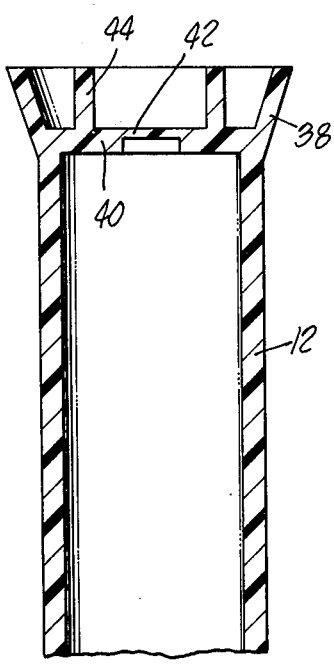
FIG. 2 is a sectional elevation view of the embodiment shown in FIG. 1 showing the piston of the assembly in the position it occupies in the rear end of the tube after it has been drawn rearwardly to create a vacuum within the tube.

FIGS. 1 and 2 illustrate one preferred embodiment of a fluid collection tube assembly constructed in accordance with the teachings of the present invention. The fluid collection tube assembly 10 includes a tube member 12 having a forward end provided with a cannula-puncturable diaphragm or stopper 14 and an open rear end 16. A piston assembly 18 comprising a piston actuator member 20 having a piston head 22 carried thereon is slidably disposed in the tube 12.

The collection tube 12 is preferably constructed of a nonbreakable material, such as injection molded plastic, for example. It is contemplated that the collection tube 12 could be a glass or plastic tube fitted with a conventional rubber stopper in the forward end thereof. However, a single piece plastic tube such as tube 12 has a number of advantages:

(1) A plastic tube is less prone to breakage, thereby preventing loss of the specimen fluid collected thereby and resultant hazards to personnel handling the tube (particularly if the specimen is diseased or contaminated).

(2) The dimensions of the tube can be held to tighter tolerances than on extruded glass tubing. This is especially true on the inside wall of the tube where the fit of the piston head 22 is critical.

Figure 8:
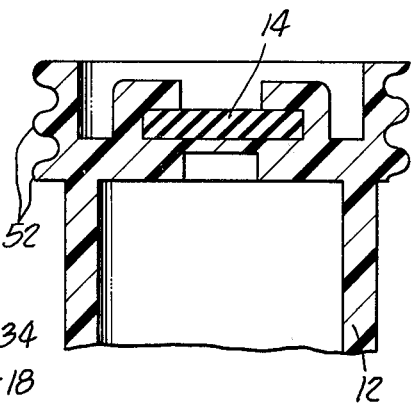
FIG. 8 is a partial sectional elevation view showing the forward end of a fluid collection tube constructed in accordance with the teachings of the present invention, wherein said forward end of the tube is provided with screw threads for receiving mating screw threads on a cover member.

The forward end of the tube may be provided with molded threaded retention rings (such as shown in FIG. 8) or snap fit rings for cooperating with mating threads or rings on a cover member (not shown).

The piston head 22 is preferably made of a resilient material, such as rubber, for example, which will form a sliding sealing engagement with the interior wall of the tube 12. As shown in FIGS. 1 and 2, the piston head 22 is provided with forward and rear annular sealing rings 24 and 26 which sealingly engage the interior wall of the tube 12.

The piston actuator member 20 is shown in FIGS. 1, 2, 4, 5 and 6. The piston actuator 20 includes a flanged head 28, a reduced-diameter neck portion 30, a generally flat base 32 and a pair of spaced tabs 34, 34 all integrally formed and preferably made of a plastic material.

As best shown in FIGS. 1 and 2, the lower end of the piston head 22 fits around the reduced neck 30 of the actuator 20, between the flanged head 28 and the base 32.

The tabs 34, 34 are biased inwardly when the piston actuator is fully disposed within the tube 12 (FIG. 1) and spring outwardly so that the bottom, curved portions 36, 36 thereof cover the rear end 16 of the tube 12 when the piston assembly 18 is withdrawn into the rear end of the tube 12 (FIG. 2).

Figure 3:
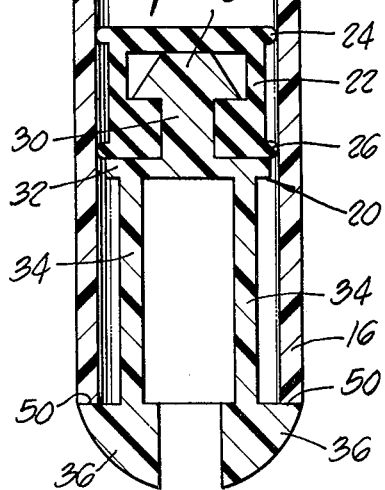
FIG. 3 is a partial sectional elevation view of the tube shown in FIGS. 1 and 2 showing the forward end of the tube before the cannula-puncturable diaphragm or stopper is applied to cover the forward end of the tube.
Figure 4:
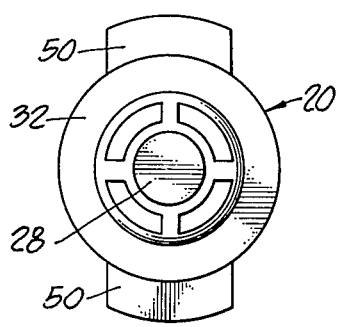
FIG. 4 is a top plan view of the piston actuator of the fluid collection tube assembly of the present invention.
Figure 5:
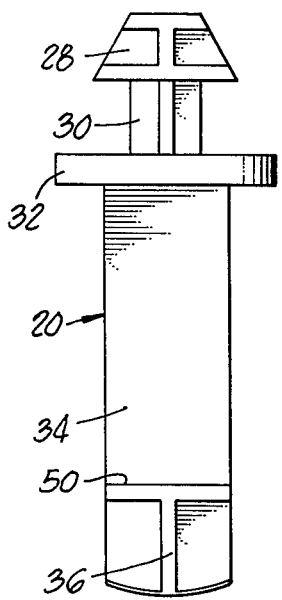
FIG. 5 is an elevation view of the piston actuator shown in FIG. 4.
Figure 6:
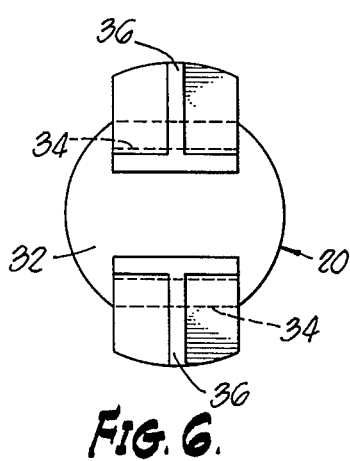
FIG. 6 is a bottom plan view of the piston actuator shown in FIGS. 4 and 5.

The forward end of the tube 12 is provided with an integral, upwardly and outwardly flaring skirt portion 38 in the embodiments shown in FIGS. 1-3. A forward end wall 40 covers the forward end of the tube 12 and is provided with a very thin wall section 42 underlying the diaphragm or stopper 14. The thin forward wall section 42 is thin enough to be easily penetrated by a needle cannula. It is contemplated that the thin wall section 42 may be eliminated so that only the stopper or diaphragm 14 covers the forward end of the chamber within the tube 12.

The stopper or diaphragm 14 is disposed within a generally annular wall 44 (FIG. 3) which has its upper or forward end bent to overlie and retain the diaphragm 14 (FIGS. 1 and 2). The stopper or diaphragm 14 is preferably made of a resilient material (e.g., rubber) which is adapted to provide a selfsealing action and close the opening made by a cannula needle (not shown) which penetrates the diaphragm 14 when fluid is to be inserted or removed from the tube 12.

FIG. 1 shows the collection tube assembly with the piston assembly 18 positioned as it would be when the assembly is delivered to the user (e.g., a hospital or doctor's office). The piston assembly 18 is positioned adjacent the closed forward end of the tube 12 with ambient air in the space between the diaphragm 14 and the piston head 22.

When it is desired to take a fluid sample from a patient, the piston assembly is drawn rearwardly, into the open rear end of the tube 12 (i.e., the position shown in FIG. 2). As the piston assembly is drawn rearwardly a vacuum is created within the tube 12 since the annular forward and rear sealing rings 24 and 26 on the resilient piston head 22 are in sliding sealing engagement with the interior wall of the tube 12.

Figure 7:
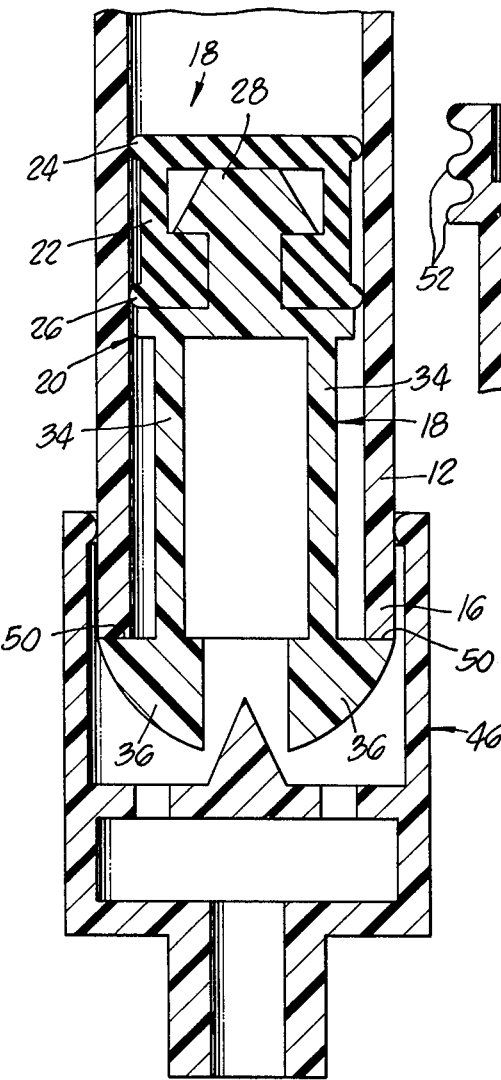
FIG. 7 is a partial elevation view showing the bottom of the fluid collection tube assembly of the embodiment shown in FIGS. 1 and 2, with the piston member disposed in the rear end of the tube and a vacuum-application adapter over the rear end of the tube for drawing the piston assembly rearwardly to create a vacuum in the tube.

FIG. 7 illustrates one method for withdrawing the piston assembly 18 into the rear end 16 of the tube 12 by using a vacuum coupling or adaptor 46. Using the adaptor 46, vacuum is applied at the rear end of the tube 12 until the piston assembly 18 is withdrawn to the position shown in FIGS. 2 and 7. In the rear position shown in FIGS. 2 and 7, the rounded ends 36, 36 on the tabs 34, 34 of the piston actuator 20 are locked in position by engaging the rear end of the tube 12.

Figure 9:
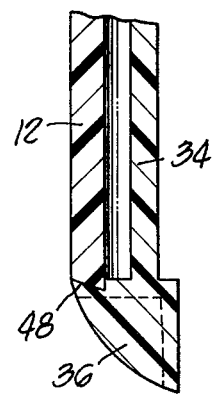
FIG. 9 is a partial sectional elevation view showing the manner in which the piston actuator member engages the rear end of the collection tube in one embodiment of the present invention to hold the piston actuator member in place in the rear end of the tube.

As shown in FIG. 9, it is contemplated that the outer periphery of each of the rounded ends 36 of each tab 34 and the annular rear end surface 48 of the tube 12 may be bevelled to more firmly lock the rounded ends 36, 36 in place.

It is contemplated, of course, that other means (i.e., other than the vacuum means described above) may be employed for withdrawing the piston assembly 18 in the tube 12 to create a vacuum in the tube. For example, it is contemplated that a tool (not shown, such as a blade type key, for example) could be inserted between the tabs 34, 34 and rotated to engage the forwardly facing surfaces 50, 50 of the rounded ends 36, 36. Such a tool could then be pulled rearwardly to pull the piston assembly 18 rearwardly in the tube 12 from the position shown in FIG. 1 to the position shown in FIG. 2 to create a vacuum within the tube. As the piston assembly reaches the position shown in FIG. 2, the tool could then be rotated to spread the tabs 34, 34 until the forwardly facing surfaces 50, 50 engage the rear end of the tube 12 (FIG. 2). Thereafter, the tool (not shown) would be withdrawn.

As shown in FIG. 2, the rounded ends 36, 36 on the tabs 34, 34 of the piston actuator 20 are shaped such that when the piston actuator is in its rear position (FIG. 2), the assembly presents a rounded rear contour similar to the bottom of a conventional glass tube. This feature also provides a tube assembly that fits conventional centrifuge cups for processing of the collected fluid.

FIG. 8 illustrates how the forward end of the tube 12 may be molded to provide external screw threads which will cooperate with complementary internal screw threads on a cover member (not shown) which may be provided to cover the forward end of the improved collection tube assembly of the present invention.

From the foregoing, it will be appreciated that the present invention provides an improved fluid collection assembly for collecting biological fluids (such as blood, for example) which may be made of plastic and which may be evacuated or vacuumized prior to use. In this regard, it has been found that when the collection tube 12 of the assembly 10 of the present invention is made of polypropylene plastic, the vacuum therein may be retained for at least four hours. Thus, it is contemplated that storage room personnel in hospitals or other medical facilities may vacuumize collection tube assemblies constructed in accordance with the teachings of the present invention (i.e., by drawing the piston assemblies 18 rearwardly in the tubes 12) before dispensing them to medical personnel (e.g., nurses). Alternatively, the tubes 12 may be vacuumized by attending medical personnel (e.g., nurses) just prior to collecting fluids from patients.

Accordingly, the improved collection tube assembly of the present invention overcomes the cost, breakage and disease transference problems associated with the use of conventional glass collection tubes while retaining the benefit of having such collection tubes vacuumized prior to use.

It will also be appreciated that the improved collection tube assembly of the present invention may be employed to dispense a collected fluid specimen without having to remove a stopper from the tube, pour collected fluid from the collection tube, or insert an eye dropper or the like into an open tube. Collected fluid may be dispensed from the collection tube assembly 10 of the present invention by inserting a needle cannula through the diaphragm or stopper 14 and forcing the piston assembly 18 forwardly in the tube 12 to dispense a fluid specimen through the needle cannula.

It is contemplated that numerous changes, modifications and/or additions may be made to the specific embodiments of the present invention shown in the drawings and described above without departing from the spirit and scope of the present invention. Accordingly, it is intended that the scope of this patent be limited only by the appended claims.

What I claim is:

1. A biological fluid sample collection tube assembly comprising:

a fluid sample receiving container having opposite ends and an interior wall defining a fluid-receiving chamber;

closure means closing one end of said container; said closure means including a cannula-puncturable member adapted to be pierced by a cannula needle for delivery of a biological fluid sample into the fluid-receiving chamber of said container;

the other end of said container being open;

a vacuum-creating member disposed within the container and spaced from said open end thereof; said vacuum-creating member having a peripheral portion in fluid sealing engagement with the interior wall of said container so that when said vacuum-creating member is moved toward said open end of said container at least a partial vacuum will be created between said cannula-puncturable member and said vacuum-creating member; said vacuum creating member including outer end portions which are rounded and which fit outside said open end of said container when said vacuum creating member is withdrawn into said open end of said container;

the space between said vacuum-creating member and said closure means being at substantially atmospheric pressure before said vacuum-creating member is moved toward said open end of said container; and means normally separated from said vacuum-creating member and adapted to be selectively placed in operative association with said vacuum-creating member for moving said vacuum-creating member toward said open end of said container to create at least a partial vacuum therein.

2. A biological fluid-receiving tube assembly, comprising:

a tubular container having an interior wall defining a fluid-receiving chamber;

said tubular member having opposite ends;

closure means closing one end of said tubular container; said closure means including a puncturable closure member adapted to be punctured by a needle cannula so that biological fluid can be introduced therethrough and into said fluid-receiving chamber;

the other end of said tubular container being open;

a vacuum-creating piston member disposed within said fluid-receiving chamber of said tubular container for selectively creating at least a partial vacuum in said chamber said vacuum-creating piston member having a generally cirular peripheral portion sealingly engaging said interior wall of said container; said vacuum-creating piston member being spaced from said open end of said container; whereby, when said vacuum-creating piston member is moved toward said open end of said container at least a partial vacuum will be created between said vacuum-creating piston member, said piston member including outer end portions which are rounded and which fit outside said open end of said container when said vacuum-creating member is withdrawn into said open end of said container;

the space between said vacuum-creating piston ,ember and said closure means, before said piston member is moved toward said open end of said container, being substantially atmospheric pressure; and means normally separated from said vacuum-creating member and adapted to be selectively placed in operative association with said vacuum-creating member for moving said vacuum-creating member toward said open end of said container to create at least a partial vacuum therein.

* * * * *